United States Patent [19]

Cline et al.

[11] Patent Number: 5,368,032
[45] Date of Patent: Nov. 29, 1994

[54] MANUALLY POSITIONED FOCUSSED ENERGY SYSTEM GUIDED BY MEDICAL IMAGING

[75] Inventors: Harvey E. Cline, Schenectady; Ronald D. Watkins, Niskayuna, both of N.Y.

[73] Assignee: General Electric Company, Schenectady, N.Y.

[21] Appl. No.: 149,485

[22] Filed: Nov. 9, 1993

[51] Int. Cl.⁵ .............................................. A61B 5/055
[52] U.S. Cl. .................................... 128/653.2; 601/3; 607/97
[58] Field of Search ............... 128/653.1, 653.2, 653.5, 128/660.3, 24 AA, 24 EL; 607/97; 601/2–4

[56] References Cited

U.S. PATENT DOCUMENTS

| | | | |
|---|---|---|---|
| 4,896,673 | 1/1990 | Rose et al. | 128/660.03 |
| 4,914,608 | 4/1990 | Lebihan et al. | 364/557 |
| 4,924,198 | 5/1990 | Laskaris | 335/216 |
| 4,984,575 | 1/1991 | Uchiyama et al. | 128/660.03 |
| 5,036,836 | 8/1991 | Terai et al. | 128/24 EL |
| 5,213,102 | 5/1993 | Kudo et al. | 128/24 EL |
| 5,247,935 | 9/1993 | Cline et al. | 128/653.2 |
| 5,271,400 | 12/1993 | Dumoulin et al. | 128/653.2 |

OTHER PUBLICATIONS

"Effects of Physical Parameters on High Temperature Ultrasound Hyperthermia" Ultrasound in Med. & Biol. vol. 16, No. 4, pp. 409–420, 1990.

Primary Examiner—Ruth S. Smith
Attorney, Agent, or Firm—Lawrence P. Zale; Marvin Snyder

[57] ABSTRACT

A manually positioned focussed energy transducer system facilitates medical procedures by allowing a physician to manually position the focal point of the focussed energy transducer to a selected tissue. The focal point of the focussed energy transducer is the location which tissue is destroyed when the energy transducer is activated. A tracking device tracks the position and orientation of the ultrasound transducer. An MR imaging system creates an image of internal structures of the patient near the location of the energy transducer. A superposition device receives the position and orientation of the ultrasound transducer from the tracking device and superimposes a symbol on the image corresponding to the position of the energy transducer relative to the patient. This allows the physician to adjust the position of the energy transducer to the appropriate location without the need for energizing the energy transducer.

4 Claims, 4 Drawing Sheets

MANUALLY POSITIONED FOCUSSED ENERGY SYSTEM GUIDED BY MEDICAL IMAGING

CROSS REFERENCE TO RELATED APPLICATIONS

This application is related to U.S. patent applications "Magnetic Resonance Guided Focussed Ultrasound Surgery" by Harvey Cline et al. Ser. No. 07/854,040 filed Mar. 19, 1992; "Magnetic Resonance Surgery Using Heat Waves Produced with Focussed Ultrasound" by Harvey Cline et al. Ser. No. 07/751,259 filed Aug. 29, 1991; "Magnetic Resonance Surgery Using Heat Waves Produced with a lo Laser Fiber" by Harvey E. Cline et al. Ser. No. 08/125,520 filed Sept. 14, 1993; U.S. Pat. No. 4,924,198 "Superconductive Magnetic Resonance Magnet without Cryogens" by Evangelos T. Laskaris issued May 8, 1990; "Open Gradient Coils for Magnetic Resonance Imaging" by William Barber et al. Ser. No. 08/146,346 filed Nov. 2, 1993; "MR Imaging System For Minimally Invasive Surgery" by Roemet et al. Ser. No. 08/146,345 filed Nov. 2, 1993; and "Automatically Positioned Focussed Energy System Guided by Medical Imaging" by Harvey Cline, Ronald Watkins Ser. No. 08/149,484 filed Nov. 9, 1993; all assigned to the present assignee and hereby incorporated by reference.

BACKGROUND OF THE INVENTION

1. Field of the Invention

The present invention relates to a system for enabling medical procedures to be performed by ultrasonic heating and more particularly to a system for enabling selective heating of tissue guided by medical imaging.

2. Description of Related Art

Conventional medical imaging provides the radiologist with internal views of a patient's anatomy. Magnetic resonance (MR) imaging provides excellent contrast between different tissues and is useful in planning surgical procedures. A tumor in a patient is much more visible in an MR image than as seen in actual surgery because the tumor and normal tissue often look similar in surgery. The tumor can also be obscured by blood during surgery.

Tumors have been selectively destroyed in cancer patients using focussed ultrasound heating at the University of Arizona, as reported by B. E. Billard, K. Hynynen and Robert. B. Roemer "Effects of Physical Parameters on High Temperature Ultrasound Hyperthermia" Ultrasound in Med. & Biol. Vol. 16, No. 4, pp. 409–420, 1990 and hereby incorporated by reference. The patient is first scanned in an MRI system to locate the tumor and plan a safe trajectory between the entry and target points. A view of the heated region is provided with the use of MR temperature sensitive pulse sequences. Known MR temperature sensitive pulse sequences are described in U.S. Pat. No. 4,914,608 "In-vivo Method for Determining and Imaging Temperature of an Object/Subject from Diffusion Coefficients Obtained by Nuclear Magnetic Resonance" by Denis LeBihan, Jose Delannoy, and Ronald L. Levin issued Apr. 3, 1990. Experiments on animals show that a heated zone above a critical temperature destroys tissue. This zone increases in size with time as the heat is applied to reach a steady state or both temperature and heat flow. If the maximum temperature is limited to 100 deg. C., then the heated zone, the area exceeding a critical temperature causing destruction of tissue, approaches 1 centimeter in diameter. It is difficult to predict the heated zone geometry because the heat flow depends on the profusion of blood as well as the tissue thermal properties.

However, it is difficult to determine the location of the energy focal point without activating the energy transducer.

Currently there is a need for a method of selectively destroying tissue non-invasively without affecting adjacent healthy tissue.

OBJECTS OF THE INVENTION

It is an object of the present invention to allow positioning of a manually operated focussed ultrasound device guided by a medical imaging device to accurately destroy selected tissue.

It is another object of the present invention to allow a physician to selectively destroy internal tissues of a patient with a small amount of invasiveness.

SUMMARY OF THE INVENTION

An energy transducer capable of focussing energy at a focal point is manually positioned by a surgeon such that the focal point is approximately located on a tissue desired to be heated. The position and orientation of the energy transducer are tracked by infrared cameras or by sensors on a mechanical arm attached to the energy transducer. The position and orientation are provided to a general purpose computer which drives a medical imaging system, such as a magnetic resonance (MR) imaging system. The MR imaging system acquires an image of structures near the energy transducer which is passed to the general purpose computer and displayed on a display means. A superposition device also receives the position and orientation of the energy transducer and superimposes a symbol on the display means indicating that position and orientation of the energy transducer. If the focal length of the energy transducer is known, the focal point may also be calculated and indicated on the display means also. This allows the physician to precisely position the focal point of the energy transducer to destroy selected tissue while leaving adjacent healthy tissue unaffected.

BRIEF DESCRIPTION OF THE DRAWINGS

The features of the invention believed to be novel are set forth with particularity in the appended claims. The invention itself, however, both as to organization and method of operation, together with further objects, may best be understood by reference to the following description taken in conjunction with the accompanying drawing in which:

DETAILED DESCRIPTION OF THE INVENTION

Figure 1:
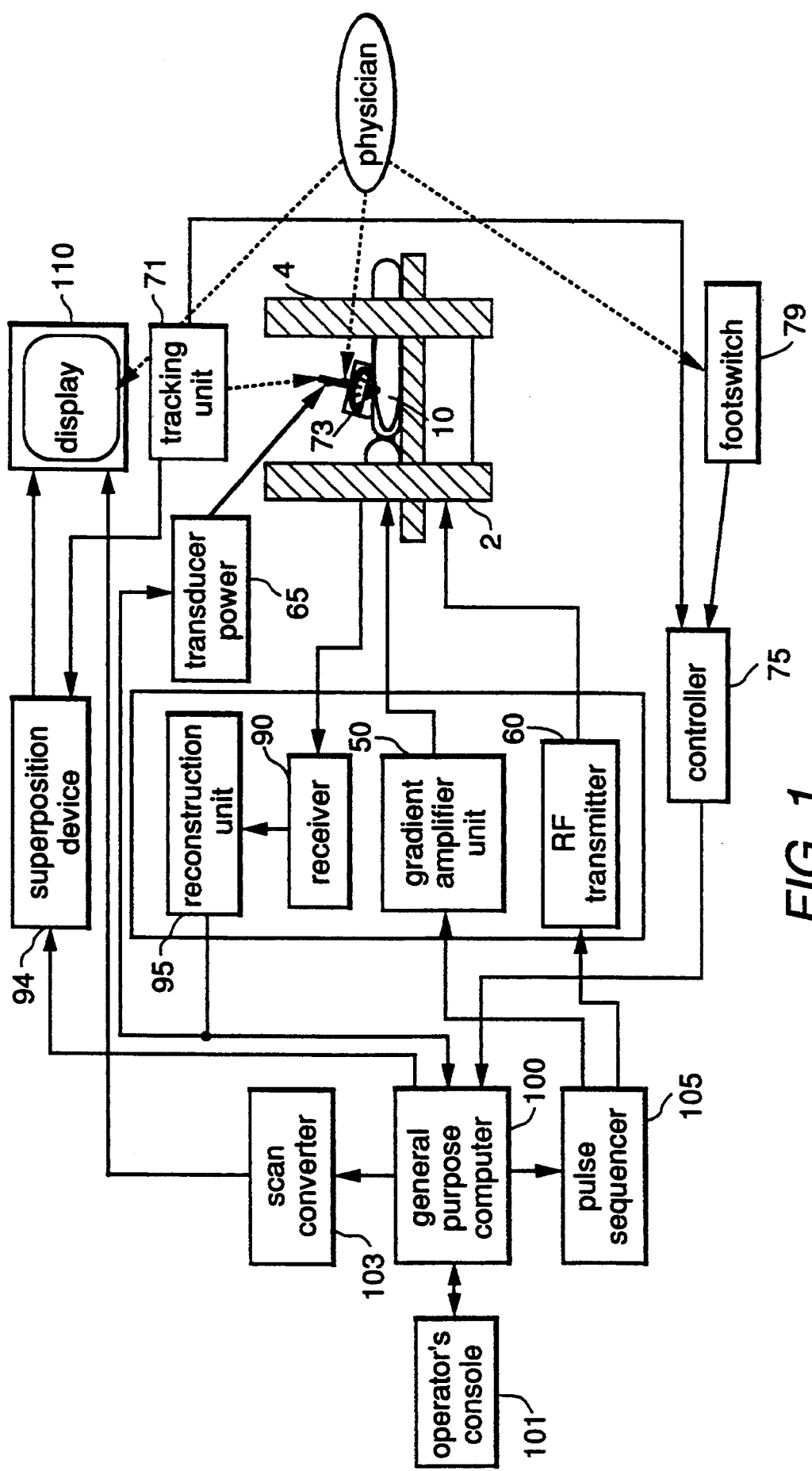
FIG. 1 is a block diagram of a first embodiment of a magnetic resonance (MR) imaging system according to the present invention.

A block diagram of the manually positioned focussed energy system guided by medical imaging of the present invention is shown in FIG. 1. In the preferred embodiment, a magnetic resonance (MR) imaging system is employed for medical imaging. A patient 10 is positioned within an open main magnet of the MR imaging system, having two superconducting rings 2, 4, is arranged as a modified "Helmholtz pair" which provides a static, spatially homogeneous magnetic field over an imaging volume between the rings. The spacing between the rings is slightly different from that of a "Helmholtz pair" in order to elongate the imaging volume, and is therefore termed a "modified Helmholtz pair". A gradient amplifier 50 provides power to a plurality of gradient coil sets located within rings 2, 4, each producing a magnetic field gradient in a specified direction. An RF transmitter 60, supplies the necessary power to RF coils to nutate nuclear spins within a patient in the imaging volume. The gradient coil sets within rings 2, 4 produce magnetic field gradients over the imaging volume without restricting access to the imaging volume, or the patient within the imaging volume.

In FIG. 1, a physician manually positions a hand-held energy transducer capable of concentrating energy on a remote focal point within the patient. Tissue in a patient can be selectively destroyed by localized heating without affecting the surrounding healthy tissue. This is disclosed in the aforementioned U.S. patent application Ser. No. 07/751,259, Cline, et al, filed Aug. 29, 1991. Energy transducer 73 may be a focussed ultrasound transducer.

The position and orientation of the energy transducer are tracked by a tracking unit 71. In the preferred embodiment, a set of infrared cameras act as a tracking unit 71 (this was manufactured by the PIXSYS corporation) and tracks the positions of two light emitting diodes (LEDs) (shown as 81 on FIG. 3) attached to the hand-held energy transducer 73. A physician locates energy transducer 73 at an approximate region of patient 10. The tracking unit 71 determines the position of the LEDs on energy transducer 73, and calculates a direction in which transducer 73 is pointing and its location. Knowing the focal length of ultrasound transducer 73, the tracking unit 71 may also calculate the position of the focal point. The physician then may trigger an image to be acquired with a device such as a footswitch 79 through a controller 75.

Controller 75 receives the location and orientation of energy transducer 73 from tracking unit 71 and provides this information to general purpose computer 100 which activates a pulse sequencer 105. Pulse sequencer 105 controls the timing and activation of gradient amplifier 50 and RF transmitter 60 to produce magnetic field gradients and RF radiation which cause an MR response signal to be emitted by tissue of patient 10 near energy transducer 73.

A receiver 90 receives the emitted MR response signal from the patient 10, and provides this signal to a reconstruction unit 95. Reconstruction unit 95 produces data for an MR image of patient 10. The image data is provided to general purpose computer 100 which displays an MR image on operator's console 101. General purpose computer 100 also provides the data to a scan convertor 103 which changes the format of the signal and provides it to a display means 110. A superposition device 94, coupled to tracking unit 71, general purpose computer 77 and display device 110, receives the position and orientation of energy transducer 73, and the field of view and image plane information from general purpose computer 100 and superimposes a symbol representing the location and position of energy transducer 73 on image of display means 110 to aid the physician in interactively positioning the energy transducer before energizing the energy transducer. This allows accurate positioning without the consequence of heating or destroying healthy tissue. When properly positioned, power is provided by a transducer power unit 65 which may be controlled by general purpose computer 100.

Display device 110 should be visible to the physician. Due to the large magnetic fields employed by MR imaging, a display means near the physician would have to be a liquid crystal display. Also since there is substantial RF radiation, it should be enclosed in a suitable RF shielding to minimize RF interference.

Figure 2:
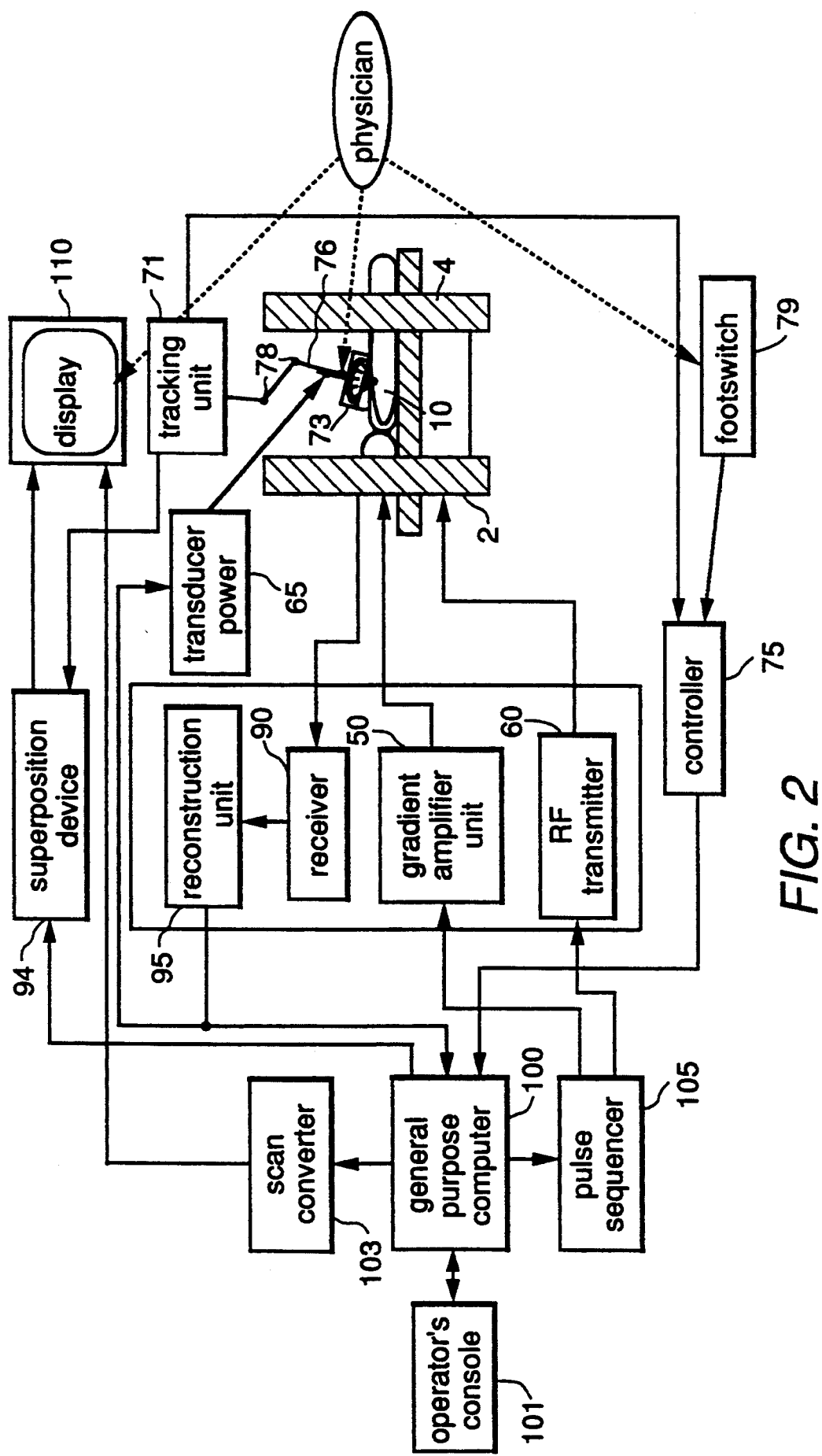
FIG. 2 is a block diagram of a second embodiment of a magnetic resonance (MR) imaging system according to the present invention.

In the embodiment of FIG. 2, a mechanical arm 76 (such as the arm manufactured by the FARO corporation) may be attached to the inner face of the magnet rings 2, 4 or otherwise fixed relative to patient 10 provide a position reference. Sensors on joints 78 of mechanical arm 76 indicate the position and orientation of energy transducer 73 attached to the end of the arm. The arm may also be equipped with locking mechanisms, to stabilize the energy transducer in a desired position when it is being energized, to limit unwanted motion, and possible injury to adjacent healthy tissue.

Footswitch 79 or other input device near the physician may also be used to control the scanner timing and provide rudimentary controls such as changing scan modes or scan type. This may be used to toggle between spin echo imaging, gradient echo imaging or any other menu of preset parameters.

The present invention may obtain images at planes through the focal point or planes bisecting an axis through the focal point and energy transducer 73 to determine intervening tissues.

The present invention may execute many types of MR imaging pulse sequences including conventional temperature-sensitive MR pulse sequences. This will allow the physician to image regions heated when energy transducer 73 is activated in addition to interval structures to selectively heat desired tissues.

Figure 3:
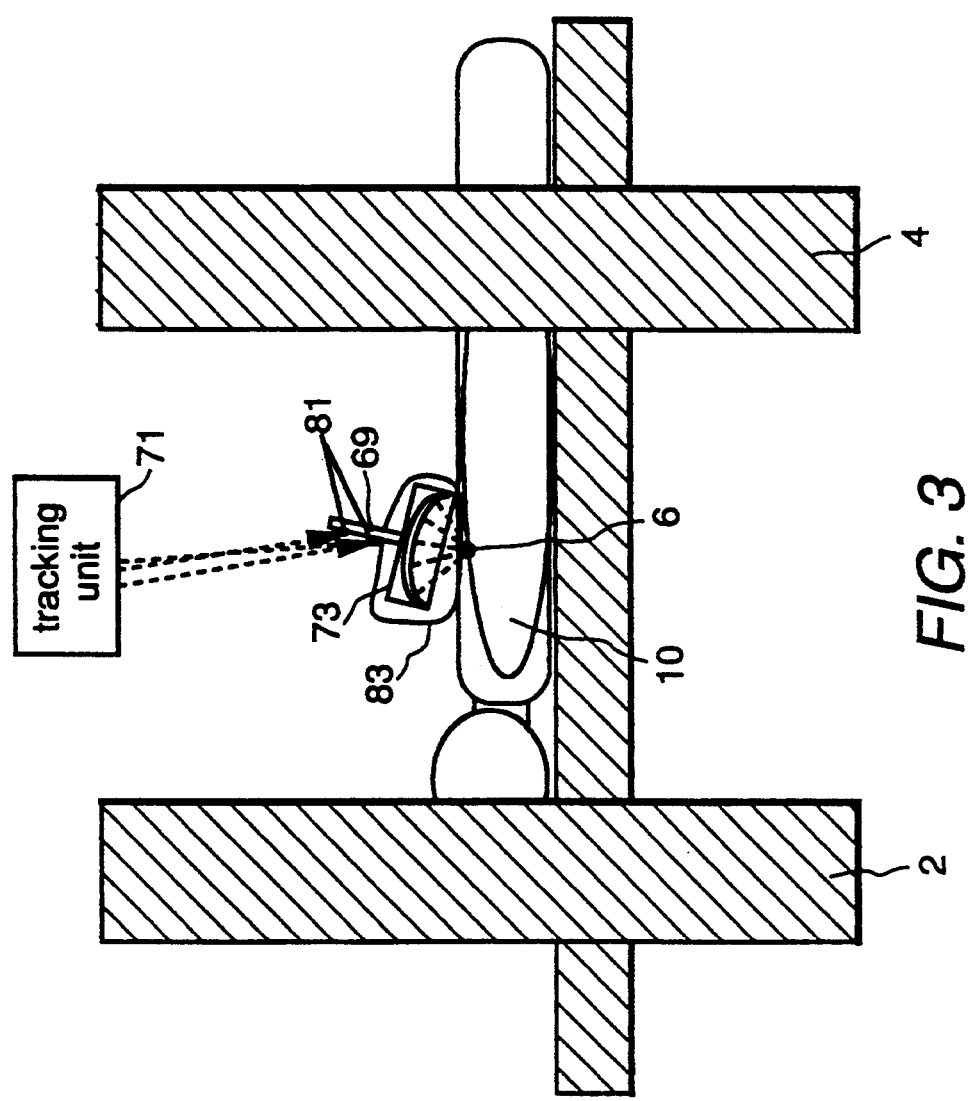
FIG. 3 is an enlarged view of the focussed energy transducer, tracking unit, and and partial MR imaging system of FIG. 1.

An enlarged view of the focussed energy transducer 73, tracking unit 71, and patient positioned within the bore of the open magnet of the MR imaging system is shown in FIG. 3. A tissues desired to be destroyed 6, such as a tumor or cyst, lies within patient 10. A physician (not shown for clarity) holds energy transducer 73 by handle 69 and positions energy transducer 73 such that the focal point is approximately on tissue 6. Energy transducer 73 is immersed energy conducting medium. In the case of energy transducer 73 being a focussed ultrasound transducer, the energy conducting medium may be water. A patient interface 83 being a membrane filled with the energy conducting medium surrounds energy transducer 73 and is placed in contact with patient 10 such that a path from energy transducer 73 to patient 10 is almost entirely energy conducting medium, except for the intervening membranes containing the conducting medium. Due to the flexible nature of patient interface 83, the physician may move energy transducer 73 to position the focal point in different locations while maintaining a path almost entirely composed of conducting medium between the energy transducer and patient 10.

Figure 4:
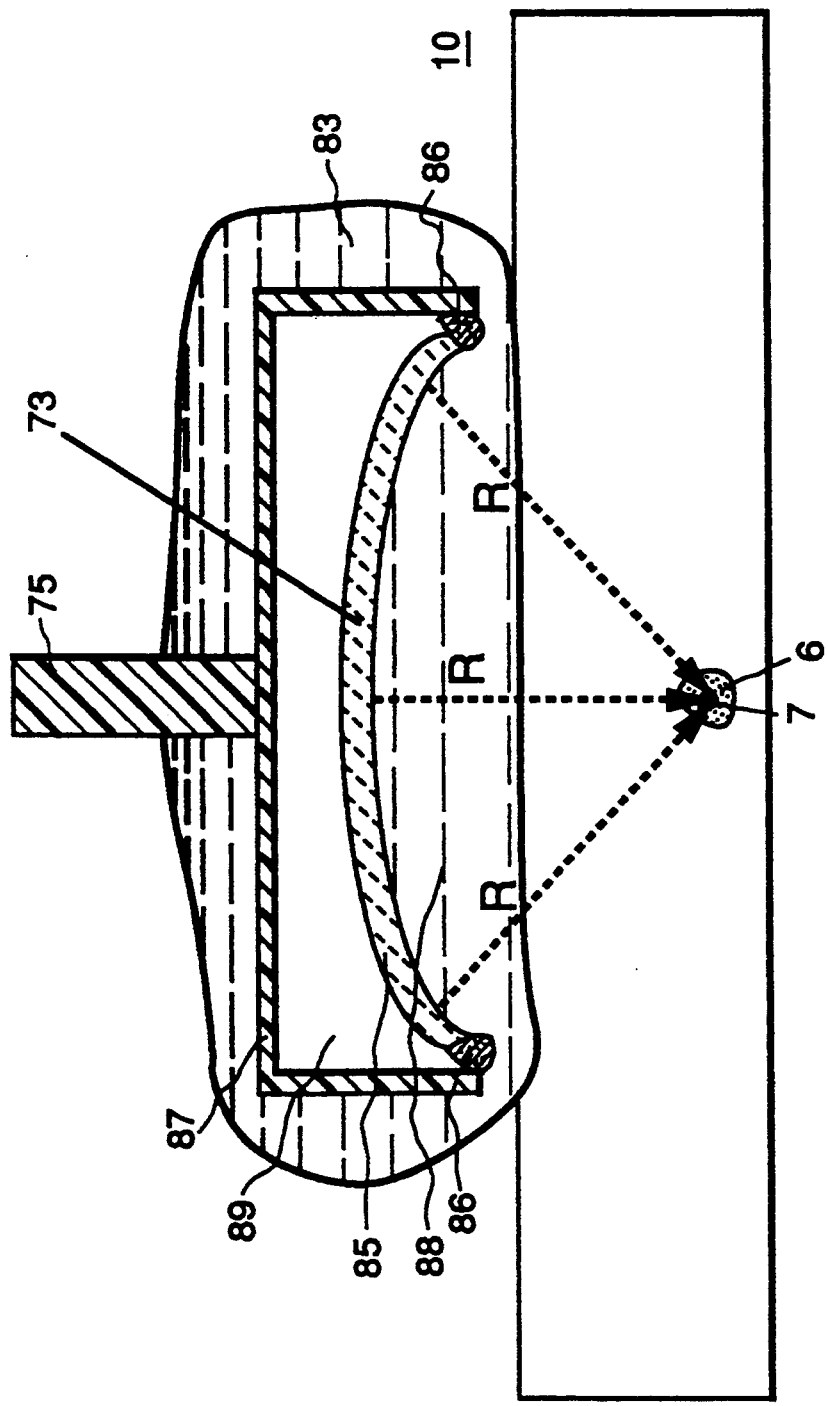
FIG. 4 is an enlarged view of the focussed energy transducer, of FIGS. 1 and 2.

FIG. 4 shows an enlarged view of energy transducer 73 and patient interface 83. Energy transducer 73 employs a piezoelectric material 74 having a concave surface. The radius of curvature is R. When activated by a signal piezoelectric material 74 creates pressure waves which pass through energy conducting material 88 in patient interface 83, and into patient 10 to create a heated region 7 at its focal point. When the energy transducer 73 is correctly positioned, the focal point falls within the tissue desired to be destroyed, shown here as tumor 6.

A casing 87 and a flexible seal 86 hold piezoelectric material 74 and creates an air gap 89 between casing 87 and piezoelectric material 74. Seal 86 may be conventional water-tight materials such as silicone. The purpose of air gap 89 is to minimize pressure waves being formed on the side opposite the focal point.

While several presently preferred embodiments of the invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A manually positioned focussed energy system for selectively heating a region of a patient, comprising:
   a) an open magnet magnetic resonance (MR) imaging system for providing an image signal from internal structures of said patient;
   b) an energy transducer for focussing energy at a focal point;
   c) tracking means for determining the position and orientation of the energy transducer;
   d) display means for displaying an image;
   e) general purpose computer coupled to the tracking means, the MR imaging system, and the display means, receiving position and orientation information of the energy transducer from the tracking means, directing the MR imaging system to acquire image signals of internal structures of the patient near the energy transducer, and providing the image signals to the display means to produce an image of the internal structures of the patient;
   f) a superposition device coupled to the tracking means and display means for receiving the position and orientation of the energy transducer and superimposing a symbol indicating the position and orientation of the focal point of the energy transducer on the image of the display means.

2. The manually positioned focussed energy system of claim 1 wherein the energy transducer comprises an ultrasound transducer.

3. The manually positioned focussed energy system of claim 1 wherein the tracking means comprises a mechanical arm attached to the energy transducer having a plurality of joints, each joint having a position sensor for measuring its current position, the arm providing the location and orientation of the energy transducer from the positions measured from the sensors.

4. The manually positioned focussed energy system of claim 1 wherein the tracking means comprises
   a) a plurality of infrared emitters fixed with respect to the energy transducer; and
   b) a plurality of infrared tracking units tracking the infrared emitters and calculating a position and orientation of the energy transducer.

* * * * *